(12) United States Patent
Harrison

(10) Patent No.: US 7,785,292 B2
(45) Date of Patent: Aug. 31, 2010

(54) INJECTION DEVICE

(75) Inventor: Nigel Harrison, Melbourn (GB)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 276 days.

(21) Appl. No.: 11/579,545

(22) PCT Filed: May 27, 2005

(86) PCT No.: PCT/GB2005/002128

§ 371 (c)(1),
(2), (4) Date: Oct. 3, 2008

(87) PCT Pub. No.: WO2005/115511

PCT Pub. Date: Dec. 8, 2005

(65) Prior Publication Data

US 2009/0054838 A1 Feb. 26, 2009

(30) Foreign Application Priority Data

May 28, 2004 (GB) ................................. 0412057.2

(51) Int. Cl.
*A61M 5/20* (2006.01)
*A61M 37/00* (2006.01)
(52) U.S. Cl. .................. 604/134; 604/131; 604/133
(58) Field of Classification Search ......... 604/134–136, 604/157
See application file for complete search history.

(56) References Cited

U.S. PATENT DOCUMENTS

| 3,543,603 A | * | 12/1970 | Gley ............................ 74/527 |
| 3,797,488 A | | 3/1974 | Hurschman et al. |
| 5,026,349 A | | 6/1991 | Schmitz et al. |
| 5,137,516 A | | 8/1992 | Rand et al. |
| 5,176,643 A | | 1/1993 | Kramer et al. |
| 5,190,526 A | * | 3/1993 | Murray et al. .............. 604/110 |
| 5,267,963 A | | 12/1993 | Bachynsky |
| 5,271,744 A | | 12/1993 | Kramer et al. |
| 5,295,965 A | | 3/1994 | Wilmot |
| 5,300,030 A | | 4/1994 | Crossman et al. |
| 5,405,362 A | | 4/1995 | Kramer et al. |
| 5,425,715 A | | 6/1995 | Dalling et al. |

(Continued)

FOREIGN PATENT DOCUMENTS

EP 1124601 B1 12/2004

(Continued)

*Primary Examiner*—Nicholas D Lucchesi
*Assistant Examiner*—Rebecca E Eisenberg

(57) ABSTRACT

The invention concerns an injection device with a housing adapted to receive a syringe having a discharge nozzle and a plunger. There is a trigger and a drive arranged to act upon the plunger on actuation of the trigger to advance the syringe from a retracted position to an extended position through an opening in the housing. A locking mechanism is arranged in and moveable relative to the housing. The locking mechanism is engaged with the plunger when the syringe is not in its extended position and disengaged from the plunger when the syringe is in its extended position. This means that movement of the plunger relative to the syringe is prevented when, in use, the syringe is advanced from a retracted position to an extended position. Hence the contents of the syringe are not expelled from the syringe during advancement from the retracted position to the extended position. The contents are only expelled when the syringe reaches the extended position.

16 Claims, 1 Drawing Sheet

U.S. PATENT DOCUMENTS

| | | |
|---|---|---|
| 5,451,210 A | 9/1995 | Kramer et al. |
| 5,478,316 A | 12/1995 | Bitdinger et al. |
| 5,487,732 A | 1/1996 | Jeffrey |
| 5,567,160 A | 10/1996 | Massino |
| 5,575,777 A | 11/1996 | Cover et al. |
| 5,599,302 A | 2/1997 | Lilley et al. |
| 5,599,309 A | 2/1997 | Marshall et al. |
| 5,681,291 A | 10/1997 | Galli |
| 5,709,662 A | 1/1998 | Olive et al. |
| 5,779,677 A | 7/1998 | Frezza |
| 5,843,036 A | 12/1998 | Olive et al. |
| 5,868,711 A | 2/1999 | Kramer et al. |
| 5,879,327 A | 3/1999 | Moreau DeFarges et al. |
| 5,913,843 A | 6/1999 | Jentzen |
| 5,954,738 A | 9/1999 | LeVaughn et al. |
| 5,957,897 A | 9/1999 | Jeffrey |
| 5,960,797 A | 10/1999 | Kramer et al. |
| 6,015,438 A | 1/2000 | Shaw |
| 6,045,534 A | 4/2000 | Jacobsen et al. |
| 6,068,614 A | 5/2000 | Kimber et al. |
| 6,077,247 A | 6/2000 | Marshall et al. |
| 6,083,197 A | 7/2000 | Umbaugh |
| 6,086,562 A | 7/2000 | Jacobsen et al. |
| 6,090,078 A | 7/2000 | Erskine |
| 6,099,503 A | 8/2000 | Stradella |
| 6,099,504 A | 8/2000 | Gross |
| 6,159,181 A | 12/2000 | Crossman et al. |
| 6,179,812 B1 | 1/2001 | Botich et al. |
| 6,186,980 B1 | 2/2001 | Brunel |
| 6,203,530 B1 | 3/2001 | Stewart, Sr. |
| 6,221,044 B1 | 4/2001 | Grecco |
| 6,258,068 B1 | 7/2001 | Kirchhofer et al. |
| 6,270,479 B1 | 8/2001 | Bergens et al. |
| 6,280,421 B1 | 8/2001 | Kirchhofer et al. |
| 6,371,939 B2 | 4/2002 | Bergens et al. |
| 6,387,078 B1 | 5/2002 | Gillespie, III |
| 6,391,003 B1 | 5/2002 | Lesch, Jr. |
| 6,428,528 B2 | 8/2002 | Sadowski et al. |
| 6,461,333 B1 | 10/2002 | Frezza |
| 6,517,517 B1 | 2/2003 | Farrugia et al. |
| 6,544,234 B1 | 4/2003 | Gabriel |
| 6,565,540 B1 | 5/2003 | Perouse et al. |
| 6,565,553 B2 | 5/2003 | Sadowski et al. |
| 6,569,115 B1 | 5/2003 | Barker et al. |
| 6,569,123 B2 | 5/2003 | Alchas et al. |
| 6,569,124 B1 | 5/2003 | Perouse |
| 6,572,581 B1 | 6/2003 | Landua |
| 6,575,939 B1 | 6/2003 | Brunel |
| 6,585,702 B1 | 7/2003 | Brunel |
| 6,589,210 B1 | 7/2003 | Rolfe |
| 6,595,957 B1 | 7/2003 | Griffiths et al. |
| 6,595,962 B1 | 7/2003 | Perthu |
| 6,607,508 B2 | 8/2003 | Knauer |
| 6,607,510 B2 | 8/2003 | Landau |
| 6,620,137 B2 | 9/2003 | Kirchhofer et al. |
| 6,638,256 B2 | 10/2003 | Jansen et al. |
| 6,641,554 B2 | 11/2003 | Landau |
| 6,641,560 B1 | 11/2003 | Bechtold et al. |
| 6,641,565 B1 | 11/2003 | Lavi et al. |
| 6,645,170 B2 | 11/2003 | Landau |
| 6,645,181 B1 | 11/2003 | Lavi et al. |
| 6,656,163 B1 | 12/2003 | Marshall et al. |
| 6,673,049 B2 | 1/2004 | Hommann et al. |
| 6,676,630 B2 | 1/2004 | Landau et al. |
| 6,689,093 B2 | 2/2004 | Landau |
| 6,692,469 B1 | 2/2004 | Weekes et al. |
| 6,699,220 B2 | 3/2004 | Rolfe |
| 6,740,062 B2 | 5/2004 | Hjertman |
| 6,743,199 B2 | 6/2004 | Shue et al. |
| 6,743,203 B1 | 6/2004 | Pickhard et al. |
| 6,746,429 B2 | 6/2004 | Sadowski et al. |
| 6,767,336 B1 | 7/2004 | Kaplan |
| 6,770,056 B2 | 8/2004 | Price et al. |
| 6,776,777 B2 | 8/2004 | Barelle |
| 6,783,509 B1 | 8/2004 | Landau et al. |
| 6,793,161 B1 | 9/2004 | Fujia et al. |
| 6,796,967 B2 | 9/2004 | Jensen |
| 6,811,548 B2 | 11/2004 | Jeffrey |
| 6,846,303 B2 | 1/2005 | Eakins et al. |
| 6,890,319 B1 | 5/2005 | Crocker |
| 6,899,698 B2 | 5/2005 | Sams |
| 6,932,793 B1 | 8/2005 | Marshall et al. |
| 6,979,316 B1 | 12/2005 | Rubin et al. |
| 7,066,907 B2 | 6/2006 | Crossman et al. |
| 7,118,553 B2 | 10/2006 | Scherer |
| 7,156,823 B2 | 1/2007 | Landau et al. |
| 2001/0049496 A1 | 12/2001 | Kirchhofer et al. |
| 2002/0072709 A1 | 6/2002 | Sadowski et al. |
| 2002/0095120 A1 | 7/2002 | Larsen et al. |
| 2003/0050609 A1 | 3/2003 | Sams |
| 2003/0060773 A1 | 3/2003 | Nguyen |
| 2003/0065286 A1 | 4/2003 | Landau |
| 2003/0078546 A1 | 4/2003 | Jensen |
| 2003/0088207 A1 | 5/2003 | Rogatchev et al. |
| 2003/0093030 A1 | 5/2003 | Landau |
| 2003/0093035 A1 | 5/2003 | Mohammed |
| 2003/0105430 A1 | 6/2003 | Lavi et al. |
| 2003/0109833 A1 | 6/2003 | Sahpe |
| 2003/0135157 A1 | 7/2003 | Saulenas et al. |
| 2003/0208164 A1 | 11/2003 | Botich et al. |
| 2003/0212362 A1 | 11/2003 | Roser |
| 2003/0212370 A1 | 11/2003 | Barrelle |
| 2003/0212380 A1 | 11/2003 | Barrelle |
| 2003/0225368 A1 | 12/2003 | Landau et al. |
| 2003/0233070 A1 | 12/2003 | De La Serna et al. |
| 2003/0236504 A1 | 12/2003 | Chen |
| 2004/0015134 A1 | 1/2004 | Lavi et al. |
| 2004/0039336 A1 | 2/2004 | Amark et al. |
| 2004/0039366 A1 | 2/2004 | MacLeod |
| 2004/0069044 A1 | 4/2004 | Lavi et al. |
| 2004/0087897 A1 | 5/2004 | Hjertman |
| 2004/0111054 A1 | 6/2004 | Landau et al. |
| 2004/0111057 A1 | 6/2004 | Wilkinson |
| 2004/0133159 A1 | 7/2004 | Haider et al. |
| 2004/0138618 A1 | 7/2004 | Mazzoni |
| 2004/0143224 A1 | 7/2004 | Field et al. |
| 2004/0153033 A1 | 8/2004 | Mazzoni |
| 2005/0011780 A1 | 1/2005 | Simon et al. |
| 2005/0020979 A1 | 1/2005 | Westbye et al. |
| 2005/0027255 A1 | 2/2005 | Lavi et al. |
| 2005/0033234 A1 | 2/2005 | Sadowski et al. |
| 2005/0035029 A1 | 2/2005 | Grob |
| 2005/0040716 A1 | 2/2005 | Schmid et al. |
| 2005/0049550 A1 | 3/2005 | Kirchhofer et al. |
| 2005/0049561 A1 | 3/2005 | Hommann et al. |
| 2005/0075608 A1 | 4/2005 | Holdgate et al. |
| 2005/0085776 A1 | 4/2005 | Hommann et al. |
| 2005/0090782 A1 | 4/2005 | Marshall et al. |
| 2005/0097238 A1 | 5/2005 | Oomori et al. |
| 2005/0101919 A1 | 5/2005 | Brunnberg |
| 2005/0124940 A1 | 6/2005 | Martin et al. |
| 2005/0125019 A1 | 6/2005 | Kudna et al. |
| 2005/0203466 A1 | 9/2005 | Hommann et al. |
| 2005/0215951 A1 | 9/2005 | Saulenas et al. |
| 2005/0222539 A1 | 10/2005 | Gonzales et al. |
| 2005/0261634 A1 | 11/2005 | Karlsson |
| 2005/0273054 A1 | 12/2005 | Asch |
| 2005/0277885 A1 | 12/2005 | Scherer |
| 2005/0277886 A1 | 12/2005 | Hommann et al. |
| 2005/0288633 A1 | 12/2005 | Jeffrey |
| 2006/0069345 A1 | 3/2006 | Anderson et al. |
| 2006/0161111 A1 | 7/2006 | Potter et al. |
| 2006/0224124 A1 | 10/2006 | Scherer |
| 2006/0258990 A1 | 11/2006 | Weber |

| | | | | | | |
|---|---|---|---|---|---|---|
| 2006/0270986 A1 | 11/2006 | Hommann et al. | WO | WO 95/35126 A1 | 11/1995 |
| 2007/0027430 A1 | 2/2007 | Hommann | WO | WO 97/13538 A1 | 4/1997 |
| 2007/0078382 A1 | 4/2007 | Hommann et al. | WO | WO 99/22789 A1 | 5/1999 |
| 2007/0142787 A1 | 6/2007 | Scherer | WO | WO 99/59658 A1 | 11/1999 |

FOREIGN PATENT DOCUMENTS

| | | | | | |
|---|---|---|---|---|---|
| FR | 1538565 A | 9/1968 | WO | WO 00/64515 A1 | 11/2000 |
| FR | 2629706 A | 10/1989 | WO | WO 03/039633 A2 | 5/2003 |
| WO | WO 88/10129 A1 | 12/1988 | WO | WO 03/051434 A2 | 6/2003 |
| WO | WO 92/19296 A | 11/1992 | WO | WO 2004/035117 A2 | 4/2004 |
| WO | WO 93/23098 A1 | 11/1993 | WO | WO 2004/047891 A1 | 6/2004 |
| WO | WO 94/04207 A1 | 3/1994 | WO | WO 2005/082438 A1 | 9/2005 |
| WO | WO 95/29720 A1 | 11/1995 | WO | WO 2005/097238 A3 | 10/2005 |

* cited by examiner

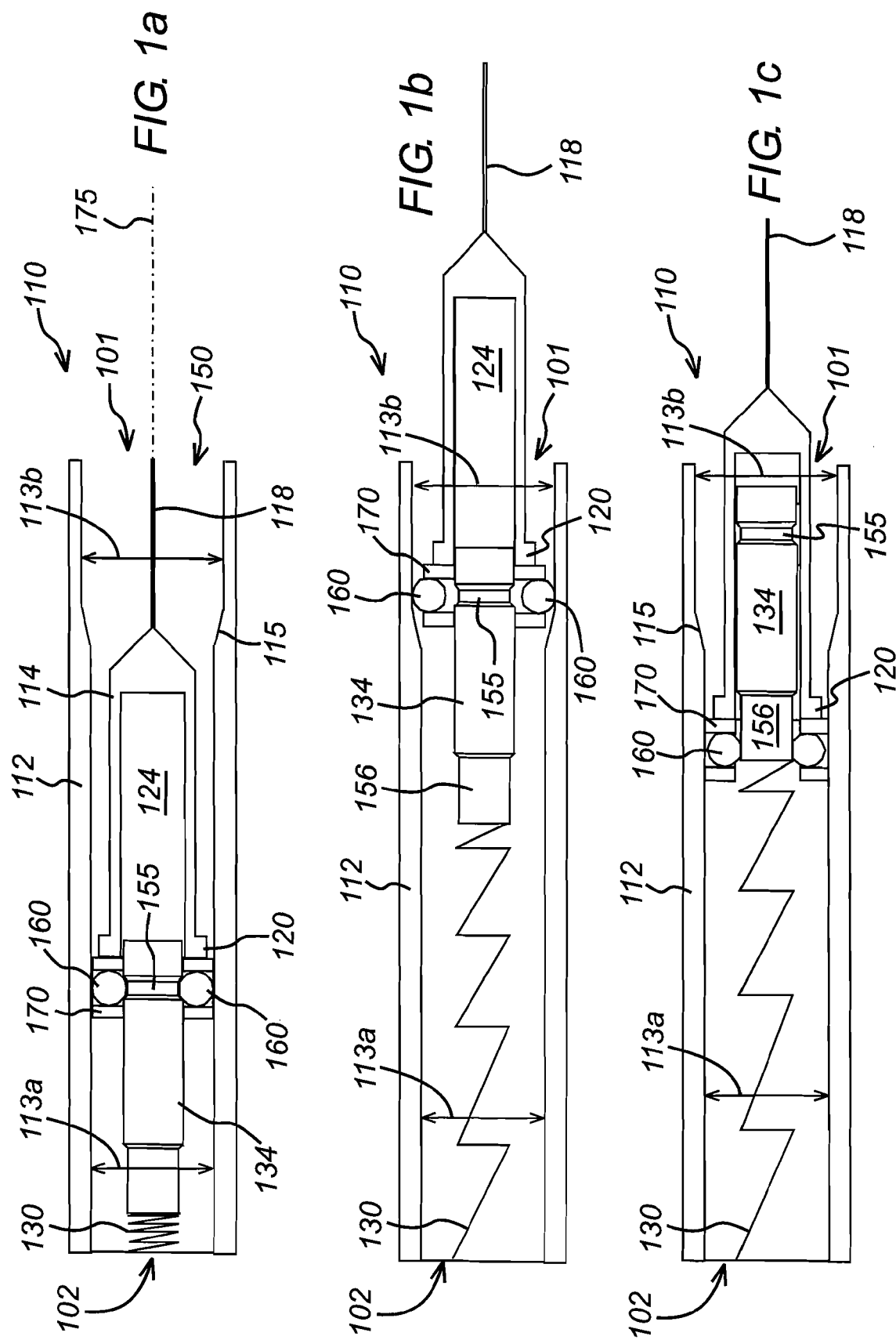

INJECTION DEVICE

FIELD OF INVENTION

The present invention relates to an injection device of the type that receives a syringe, extends it and discharges its contents. Devices of this general description are shown in WO 95/35126 and EP-A-0 516 473 and generally comprise a syringe in a housing with a drive spring that can be released by actuation of a trigger. Depression of the trigger causes the drive spring to become operative.

BACKGROUND OF INVENTION

The first automatic action of current injection devices is to drive a syringe forward and push a needle of the syringe into the patient. This is achieved by applying a force to either the syringe body ("direct drive") or the syringe piston ("piston drive"). Piston drive is a simpler approach to engineer as one mechanism can be used to drive the needle out and then expel the contents of the syringe. However, this approach does carry a risk that a small quantity of the fluid may be expelled before the needle has reached a required depth in a patient's skin. The system relies on the needle reaching full depth before a significant quantity of fluid can be expelled. The rate of fluid delivery is limited by the force available, the viscosity of the fluid and the restriction of the needle. This property has sometimes been described as hydraulic lock.

It is therefore an aim of the present invention to provide an injection device utilising a piston drive approach which does not expel any fluid before a needle has reached a required depth in a patient's skin. As ever, the simplest and cheapest way of achieving this is sought.

SUMMARY OF THE INVENTION

In view of the foregoing, according to the present invention, there is provided an injection device, comprising: a housing adapted to receive a syringe having a discharge nozzle; and a drive arranged on actuation to advance the syringe from a retracted position to an extended position through an opening in the housing and discharge the contents of the syringe, characterised by a locking mechanism which engages the drive with the syringe when the syringe is not in its extended position and which is disengaged from the drive and engages the syringe with the housing when the syringe is in its extended position such that movement of the drive relative to the syringe is prevented when the syringe is advanced from its retracted position to its extended position and movement of the housing relative to the syringe is prevented when the syringe is in its extended position and its contents are being discharged. Hence, when the drive is locked to the syringe, the contents of the syringe are not ejected through the discharge nozzle as the syringe is moved from its retracted to its extended position. Furthermore, when the syringe is in its extended position and its contents are being discharged, the syringe is locked to the housing so that it cannot be forced back into the housing by an external force as its contents are being discharged, for example by the contact force between a patient and their skin.

In one embodiment of the present invention, an injection device according to claim 1, wherein an inner surface of the housing defines at least a first cross-section and a second cross-section of the housing with a first internal diameter and a second internal diameter respectively, the first diameter being less than the second diameter and the second cross-section located adjacent the opening; wherein the drive comprises a first detent; and wherein the locking mechanism comprises at least one movable locking member positioned between the inner surface and the drive, such that the locking member is engaged in the first detent when positioned between the inner surface and drive in the first cross-section and is disengaged from the first detent when positioned in the second cross-section. This arrangement provides a simple locking mechanism which is simple to manufacture.

Preferably, the first detent is a channel in an outer surface of the drive. If the drive is cylindrical, the channel may extend around the circumference of the drive.

Preferably, when located in the first cross-section, the locking member acts on a flange of the syringe located at an end of the syringe opposite the discharge nozzle. Thus, a conventional syringe can be utilised in the injection device.

Advantageously, the injection device comprises a support member arranged to constrain the locking member against the flange of the syringe. The locking mechanism acts on the support member which then acts on the syringe.

In one embodiment of the present invention, the support member is a sleeve surrounding the drive. Preferably, the sleeve comprises an outer surface and an inner surface and an opening between its inner surface and its outer surface dimensioned to support the locking member. The sleeve can easily be positioned around the drive during manufacture.

The first cross-section and second cross-section are preferably separated by a step in the inner surface, such that the location of the step in the inner surface defines the location at which the locking mechanism is disengaged from the plunger as the drive advances the syringe from the retracted position to the extended position. The step may be ramped between the first cross-section and the second cross-section.

Preferably, each locking member is a ball which allows the locking member to freely rotate as the plunger moves relative to the housing and syringe.

Advantageously, the edges of the first detent are bevelled to allow the balls to move in and out of the channel easily.

In one embodiment of the present invention, the locking mechanism is arranged in communication with the drive such that it becomes disengaged from the housing when the syringe is in its extended position when the contents of the syringe have been discharged, thereby permitting the syringe to be moved from its extended position to its retracted position. Thus, the syringe does not remain locked in its extended position and can be safely retracted into the housing of the syringe.

Preferably, the drive may comprise a second detent at the end of the drive furthest from the opening such that when the second detent is positioned adjacent the locking member when the contents of the syringe have been discharged, the locking member becomes positioned in the first cross-section, thereby disengaging the locking mechanism from the housing and permitting the syringe to be moved from its extended position to its retracted position.

The injection device may comprise a return drive arranged to act upon the syringe after the contents of the syringe have been discharged to withdraw the syringe from the extended position to the retracted position. This way, the syringe can be automatically retracted into the housing after discharge of its contents. The locking mechanism ensures that retraction does not occur until the drive has reached a certain pre-defined position relative to the syringe.

Advantageously, the drive may be a plunger of the syringe.

BRIEF DESCRIPTION OF THE DRAWINGS

The invention will now be described by way of example with reference to the accompanying drawings, in which:

FIG. 1a shows in section an injection device of the type to which the present invention is applicable with a syringe retracted before discharge of its contents;

FIG. 1b shows in section the injection device of FIG. 1a with the syringe fully extended before discharge of its contents; and FIG. 1c shows in section the injection device of FIG. 1a with the syringe fully extended after discharge of its contents.

DETAILED DESCRIPTION OF THE DRAWINGS

FIG. 1a shows an injection device 110 according to the present invention. The injection device 110 has a housing 112 which has a first internal cross-section 113a and a second internal cross-section 113b. The injection device 110 has a proximal end 101 and a distal end 102. The first cross-section 113a has a diameter which is less than the diameter of the second cross-section 113b. The change in diameter between the first cross-section 113a and the second cross-section 113b is defined by a step 115 which is a continuous slope line (i.e. a ramp) between the inner surfaces of the first and second cross-sections 113a, 113b. A syringe 114 of conventional hypodermic type is slidably mounted inside the housing 112. The housing 112 has a proximal end 101 and a distal end 102. At the proximal end 101 of the housing 112 is an opening 150 through which the syringe 114 is moved from a retracted position inside the housing 112 into an extended position outside the housing 112. The second cross-section 113b is located nearer to the proximal end 101 than the distal end 102 of the housing 112.

The syringe 114 includes a discharge nozzle which is shown terminating at one end in a hypodermic needle 118 and at the other in a flange 120. The conventional plunger and bung that would normally be used to discharge the contents of the syringe 114 manually have been removed and replaced with a drive 134 which is essentially of the form of a plunger and has a bung on its end which is inserted into the syringe 114. The drive also comprises resilient biasing means connected at one end to the distal end 102 of the housing and at its other end to the end of the plunger which is not inserted into the syringe 112. The resilient biasing means here takes the form of a compression drive spring 130. This drive element 134 constrains a drug 124 to be administered within the syringe body 116. Whilst the syringe 114 illustrated is of hypodermic type, this need not necessarily be so. Transcutaneous or ballistic dermal and subcutaneous syringes may also be used with the injection device of the present invention.

Drive from the drive spring 130 is transmitted via the drive element 134 to the syringe 114 to advance it from its retracted position (as shown in FIG. 1a) to its extended position (as shown in FIG. 1b) and discharge its contents through the needle 118. The drive element 134 accomplishes this task by acting directly on the drug 124 and the syringe 114.

A channel 155 is located about the circumference of the drive element 134 in the end of the drive element 134 nearest the proximal end 101 of the housing 112. Locking members are provided in the housing 112 which, in FIGS. 1a to 1c, are balls 160 located between the drive element 134 and the inner surfaces of the housing 112. The housing 112, balls 160, drive element 134 and channel 155 are all dimensioned such that when the balls 160 and drive element 134 are located in the first cross-section 113a, the balls 160 must sit in the channel 155. Here, the balls 160 are free to rotate, but remain fixed relative to the drive element 134. When the balls 160 and drive element 134 are located in the second cross-section 113b, the balls 160 need not be located in the channel 160 and are free to move out of the channel 155 in a perpendicular direction to a longitudinal axis 175 of the housing 112. Indeed, the channel 155 is bevelled such that the force applied to the drive 134 by the spring 130 forces the balls 160 out of the channel 155 into the gap created between the balls and the inner surface of the housing 112 from the increase in cross-sectional area between the first cross-section 113a and the second cross section 113b. Here, the balls 160 and drive element 134 can move relative to each other since the balls 160 are no longer held in the channel 155. Hence, the drive spring 130 is able to act on the drive 134 and force it through the syringe 114 discharging its contents. At the same time, since the balls 160 have been forced outwards by the drive 134 into the second cross-section 113b, they are unable to move back into the first cross-section 113a and therefore act to lock the syringe in its extended position (see FIG. 1b).

A support member 170 is located around the balls 160. The support member 170 takes the form of a ring which has is positioned over the drive element 134. The ring is free to slide over the drive element 134. The ring has an inner surface and an outer surface and, for each ball, there is an opening in the form of a hole between the outer and inner surfaces in which the ball is positioned.

As mentioned above, when the balls 160 are located in the first cross-section 113a, they are locked into the channel 155. Hence, as shown in FIG. 1a, when the drive spring is released by a trigger (not shown) force from the drive spring 130 against the drive element 134 is transmitted via the channel 155, through the balls 160 and support member 170 into the flange 120 of the syringe 114 to cause the syringe 114 to slide from its retracted position out of the opening 150 towards its extended position without the drive element 134 and syringe 114 moving relative to each other. Therefore, drug 124 is not expelled from the syringe 114 during advancement of the syringe 114 from its retracted position to its extended position.

When the balls 160 reach the second cross-section 113b (i.e. when the syringe 114 is in its extended position), they are free to move out of the channel 155 in a perpendicular direction to the longitudinal axis 175 of the housing 112, thus becoming disengaged from the channel 155. This is shown in FIG. 1b.

The step 115 is located such that the syringe 114 will be in its extended position when the balls 160 reach the step 115.

Now the force from the drive spring 130 in a direction parallel to the longitudinal axis 175 is applied mainly to the drive element 134 and not to the flange 120. Hence, the drive element 134 will slide in the syringe 114 and expel the drug 124 through the needle 118.

When the syringe 112 is in its extended position (as shown in FIG. 1b), the balls are forced against the inner surface of the second cross-section 112. Any force along the syringe 112 from the proximal end 101 in the direction of the distal end 102 is transmitted through the flange 120 to the balls 160 which are locked out against the step 115. In this way, the syringe 112 is prevented from moving from its extended position to its retracted position whilst its contents are being discharged.

The drive element 134 has a detent 156 at its end which is not inserted into the syringe 112 which is of narrower cross-section than its main body. When the detent 156 reaches the second cross section 113b, the balls 160 are no longer forced against the inner surface of the housing 112 (as shown in FIG. 1c). Force along the syringe 112 from the proximal end 101 in the direction of the distal end 102 causes the syringe 112 to move from an extended position to a retracted position. This force is applied by a return drive spring (not shown).

It will of course be understood that the present invention has been described above purely by way of example and modifications of detail can be made within the scope of the invention.

The invention claimed is:

1. An injection device, comprising:
   a housing adapted to receive a syringe having a discharge nozzle;
   a drive arranged on actuation to advance the syringe from a retracted position to an extended position through an opening in the housing and discharge the contents of the syringe; and
   a locking mechanism which engages the drive with the syringe when the syringe is not in its extended position and which is disengaged from the drive and engages the syringe with the housing when the syringe is in its extended position such that movement of the drive relative to the syringe is prevented when the syringe is advanced from its retracted position to its extended position and movement of the housing relative to the syringe is prevented when the syringe is in its extended position and its contents are being discharged.

2. An injection device according to claim 1, wherein an inner surface of the housing defines at least a first cross-section and a second cross-section of the housing with a first internal diameter and a second internal diameter respectively, the first diameter being less than the second diameter and the second cross-section located adjacent the opening; wherein the drive comprises a first detent; and wherein the locking mechanism comprises at least one movable locking member positioned between the inner surface and the drive,
   such that the locking member is engaged in the first detent when positioned between the inner surface and drive in the first cross-section and is disengaged from the first detent when positioned in the second cross-section.

3. An injection device according to claim 2, wherein the first detent is a channel in an outer surface of the drive.

4. An injection device according to claim 2, wherein, when located in the first cross-section, the locking mechanism acts on a flange of the syringe located at an end of the syringe opposite the discharge nozzle.

5. An injection device according to claim 4, further comprising a support member arranged to constrain the locking member against the flange of the syringe.

6. An injection device according to claim 5, wherein the support member is a sleeve surrounding the drive.

7. An injection device according to claim 6, wherein the sleeve comprises an outer surface and an inner surface and an opening between its inner surface and its outer surface dimensioned to support the locking member.

8. An injection device according to claim 2, wherein the first cross-section and second cross-section are separated by a step in the inner surface, such that the location of the step in the inner surface defines the location at which the locking mechanism is disengaged from the drive as the syringe is advanced from its retracted position to its extended position.

9. An injection device according to claim 8, wherein the step is ramped between the first cross-section and the second cross-section.

10. An injection device according to claim 2, wherein the edges of the first detent are bevelled.

11. An injection device according to any one of claims 2 to 10, wherein each locking member is a ball.

12. An injection device according to claim 2, wherein the drive comprises a second detent at the end of the drive furthest from the opening such that when the second detent is positioned adjacent the locking member when the contents of the syringe have been discharged, the locking member becomes positioned in the first cross-section, thereby disengaging the locking mechanism from the housing and permitting the syringe to be moved from its extended position to its retracted position.

13. An injection device according to claim 1, wherein the drive is a plunger of the syringe.

14. An injection device according to claim 1, wherein the locking mechanism is arranged in communication with the drive such that it becomes disengaged from the housing when the syringe is in its extended position when the contents of the syringe have been discharged, thereby permitting the syringe to be moved from its extended position to its retracted position.

15. An injection device according to claim 14, further comprising a return drive arranged to act upon the syringe after the contents of the syringe have been discharged to withdraw the syringe from the extended position to the retracted position.

16. An injection device according to claim 2 comprising a plurality of locking members.

* * * * *